(12) United States Patent
Tsao et al.

(10) Patent No.: US 8,252,575 B2
(45) Date of Patent: Aug. 28, 2012

(54) **NEWLY ISOLATED BACTERIOPHAGE SPECIFIC TO *KLEBSIELLA PNEUMONIAE***

(75) Inventors: Nina Tsao, Kaohsiung (TW); Chih-Hsin Hung, Kaohsiung (TW); Chih-Feng Kuo, Kaohsiung (TW)

(73) Assignee: I-Shou University, Kaohsiung County (TW)

( * ) Notice: Subject to any disclaimer, the term of this patent is extended or adjusted under 35 U.S.C. 154(b) by 0 days.

(21) Appl. No.: 12/986,950

(22) Filed: Jan. 7, 2011

(65) Prior Publication Data

US 2011/0217756 A1    Sep. 8, 2011

(30) Foreign Application Priority Data

Mar. 2, 2010  (TW) ............................... 99105992 A

(51) Int. Cl.
*C12Q 1/70*   (2006.01)
*C12Q 1/68*   (2006.01)
*A61K 39/108* (2006.01)
*A01N 63/00*  (2006.01)

(52) U.S. Cl. ........ 435/235.1; 435/5; 435/6.15; 424/93.6; 424/259.1

(58) Field of Classification Search ................... None
See application file for complete search history.

(56) References Cited

U.S. PATENT DOCUMENTS 6,121,036 A * 9/2000 Ghanbari et al. .......... 435/235.1
7,459,272 B2  12/2008 Morris et al.
7,807,149 B2  10/2010 Soothill et al.

OTHER PUBLICATIONS

Verma et al. (Current Microbiology. Sep. 2009; 59: 274-281).*

* cited by examiner

*Primary Examiner* — Shanon A Foley
(74) *Attorney, Agent, or Firm* — Muncy, Geissler, Olds & Lowe, PLLC

(57) ABSTRACT

A newly isolated lytic bacteriophage specifically against *Klebsiella pneumoniae*, deposited at DSMZ-Deutsche Sammlung von Mikroorganismen and Zellkulturen with deposit number (DSM 24329), shows broad host ranges and lytic effects on *K. pneumoniae* isolated from Taiwan under either in vivo or in vitro models.

9 Claims, 8 Drawing Sheets

NEWLY ISOLATED BACTERIOPHAGE SPECIFIC TO *KLEBSIELLA PNEUMONIAE*

BACKGROUND OF THE INVENTION

1. Field of the Invention

The present invention relates to a newly isolated lytic bacteriophage, particularly to a newly isolated lytic bacteriophage against *Klebsiella pneumoniae*.

2. Description of the Related Art

*Klebsiella pneumoniae*, belonging to the family of Enterobacteriaceae, is a gram-negative bacterium widely found in the normal flora of the intestinal and respiratory tracts of humans. However, the *K. pneumoniae* is also a significant opportunistic pathogen, usually causing severe diseases such as septicemia and pneumonia in immunocompromised individuals or nosocomial patients. Generally, the clinical *K. pneumoniae* infections are primary characteristics of liver necrosis, multiple cavities and edema, and are usually accompanied by symptoms like chest pain, cough, and even respiratory failure in serious cases. In recent decades, an increasing amount of *K. pneumoniae* infected patients in Taiwan have developed serious complications of pyogenic liver abscess, metastatic meningitis and endophthalmitis, particular to diabetes mellitus and chronic respiratory cases. In these situations, even if given proper treatment, most patients still struggle against the annoying complications and high mortality risk.

Traditionally, the treatment of the *K. pneumoniae* infections is mainly based on antibiotics, such as aminoglycosides (including gentamicin, tobramycin and amikacin) and cephalosporins. Nevertheless, due to multiple occurrences of *K. pneumoniae* strains currently, the therapy of *K. pneumoniae* infections has become more difficult and essential. Thus, it is crucial for clinical medicine to develop a new therapy for patients who suffer from drug-resistant strains and serious complications, in order to substitute the antibiotics treatment for controlling the *K. pneumoniae* infections.

An alternative therapeutic strategy is bacteriophage treatment, which involves providing bacteriophages against the related bacterial infection. This type of treatment has no risk of drug-resistance or abuse of antibiotics. In general, the bacteriophages will specifically infect the target bacteria, reproduce in the target bacteria and release from them, leading to serious damage to the target bacteria. Through the bacteriophage treatment, the therapy of bacterial infections can be achieved more economically, effectively and safely.

Although bacteriophage therapy has been widely applied to treat various bacterial infections, it is reported that most bacteriophages show narrow host range and specifically infection to particular bacteria only; therefore, the isolated bacteriophage nowadays may not be beneficial to treat *K. pneumoniae* infections. As a result, regarding the severe *K. pneumoniae* infections and its complications in Taiwan, there is an urgent need of isolating a new strain of bacteriophage for specifically inhibiting the invasive strain of *K. pneumoniae* in Taiwan.

SUMMARY OF THE INVENTION

The primary objective of this invention is to provide a newly isolated lytic bacteriophage specifically against *K. pneumoniae*, so as to be specifically infectious and lytic to the *K. pneumoniae* in Taiwan.

The secondary objective of this invention is to provide a newly isolated lytic bacteriophage specifically against *K. pneumoniae*, which can effectively inhibit the reproduction of *K. pneumoniae* whether in in vivo or in vitro models.

Another objective of this invention is to provide a newly isolated lytic bacteriophage specifically against *K. pneumoniae*, which can be put to use on the development of therapeutic and prophylactic medication/disinfectant for the treatment of *K. pneumoniae* infection.

A newly isolated lytic bacteriophage specifically against *Klebsiella pneumoniae*, deposited at DSMZ-Deutsche Sammlung von Mikroorganismen and Zellkulturen, at the address, Inhoffenstrasse 7B, D-38124 Braunschweig Germany, with the deposit number DSM 24329, shows broad host ranges and lytic effects to the *K. pneumoniae* isolated from Taiwan either in in vivo or in vitro models.

Further scope of the applicability of the present invention will become apparent from the detailed description given hereinafter. However, it should be understood that the detailed description and specific examples, while indicating preferable embodiments of the invention, are given by way of illustration only, since various more will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

In the various figures of the drawings, the same numerals designate the same or similar parts.

DETAILED DESCRIPTION OF THE INVENTION

The present invention relates to a newly isolated lytic bacteriophage isolated from the sewage of a hospital in Taiwan, which has been proved to show broad host range and lytic effects to *K. pneumoniae* in Taiwan whether in in vivo or in vitro models. It is suggested that the newly isolated lytic bacteriophage of the present invention is sufficient to be put to use on the development of medication or disinfectant adapted to the therapy or prophylaxis of clinical *K. pneumoniae* infections.

Figure 1:
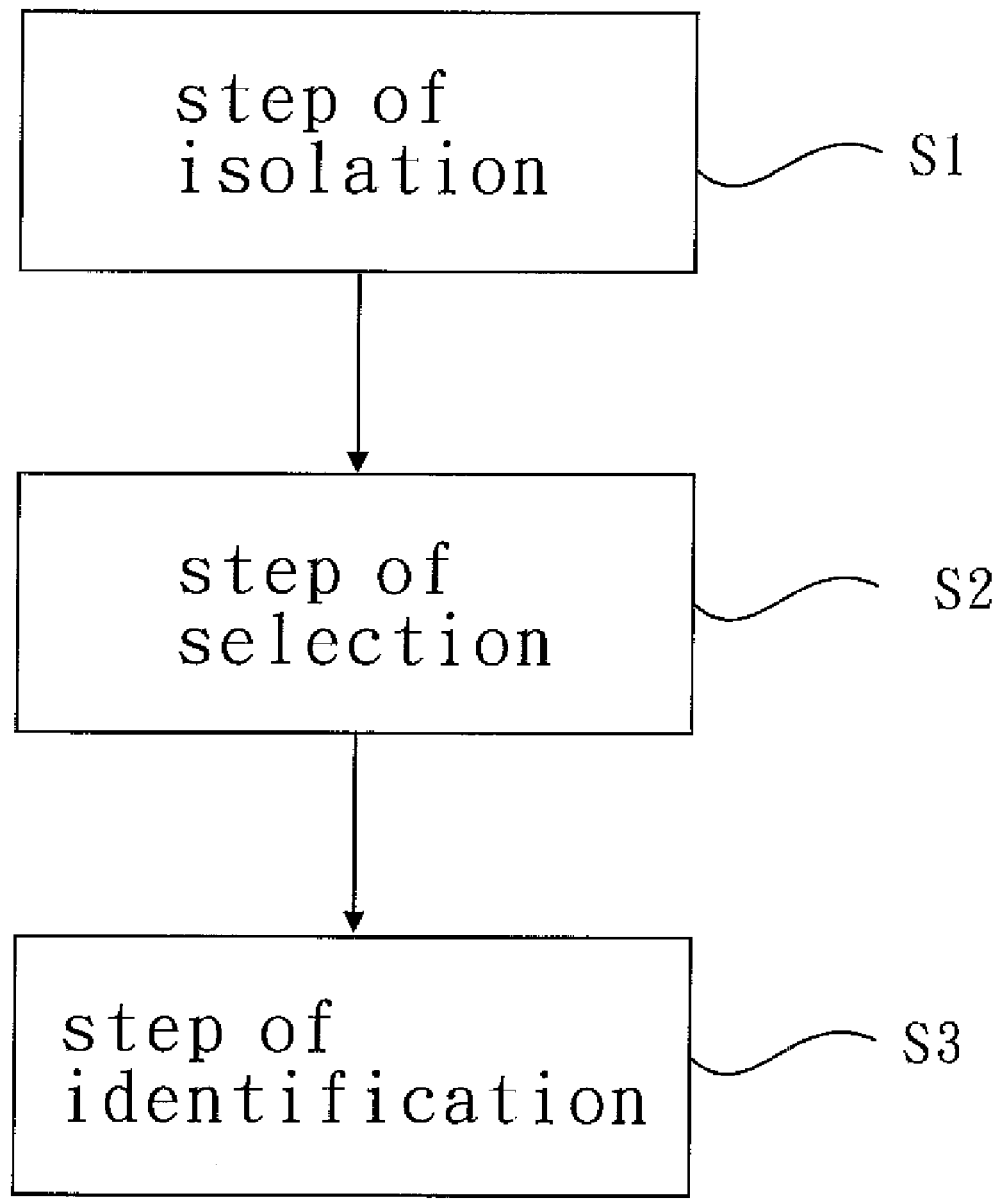
FIG. 1 is a diagram illustrating a selecting process of the newly isolated lytic bacteriophage in the present invention.

Referring to FIG. 1, in accordance with an isolation program of the newly isolated lytic bacteriophage in the present invention, the isolation program comprises a step of "isolation S1," a step of "selection S2," and a step of "identification S3".

In the step of "isolation S1," a bacteriophage specifically against *K. pneumoniae* is isolated from a sample. Precisely, the above bacteriophage is isolated from the sewage of the E-Da Hospital in Taiwan. First, a procedure of bacteriophage enrichment is performed by removing the dust, debris and germs in the sewage via a process of centrifugation at 14170×g for 15 minutes and a process of filtration with a filter of 0.22 μl, and further mixing up the sewage with a culture medium (for example LB broth) containing a clinical strain of *K. pneumoniae* (deposited at DSMZ-Deutsche Sammlung von Mikroorganismen and Zellkulturen with deposit number DSM 24328). In the present invention, the clinical strain of *K. pneumoniae* (DSM 24328) is collected from a *K. pneumoniae* infected patient in a Taiwanese hospital who has serious liver abscess and bacteremia. The sewage and the culture medium are co-incubated at 37° C. for about 12 hours to obtain a mixture. In this situation, the bacterial bacteriophages in the sewage will randomly adhere to the *K. pneumoniae* cells for infection and proliferation. Next, the mixture is extracted with chloroform (32 μl/ml), in order to lyse the *K. pneumoniae* cell and release the reproduced bacteriophages. Finally, the mixture is centrifugated at 14170×g for another 15 minutes, to remove the bacterial dregs and collect the bacteriophage lysate supernatant from the mixture.

In the step of "selection S2," a bacteriophage with specific lysis effect on *K. pneumoniae* cells is selected. Precisely, the bacteriophage is selected according to a plaque assay published by Jensen et. al. in 1998. The prepared bacteriophage lysate supernatant and an overnight culture of *K. pneumoniae* cells in a ratio of 1:1 volume, are mixed in 5 ml of soft agar (such as LB-soft agar), and poured on an agar-medium plate, for example a LB agar-plate, for overnight culturing. Then, a plurality of single plaques harvested on the medium plate will be collected and diluted with a buffer, such as a phosphate buffer. In the present invention, the diluted plaques are further mixed up with the overnight culture of *K. pneumoniae* cells and follow above steps to purified bacteriophage, and the above plaque assay is repeated for at least 3 times, finally to obtain a pure strain of bacteriophage.

After that, the pure strain of bacteriophage is amplified in *K. pneumoniae* cells according to a reproducing method reported by Langley et. al. in 2003, by co-incubating with 5 times the volume of *K. pneumoniae* cells and 50 times the volume of soft agar (such as LB-soft agar), and pouring on a medium plate for 6 hours of culturing. Then, clear plaques harvested on the medium plate will be taken and extracted in the following steps. In the present invention, the titer of the co-incubated bacteriophage and *K. pneumoniae* cells is $2\times10^8$ PFU/ml and $2\times10^9$ CFU/ml, respectively.

After the culturing, an extracted buffer, for example a PBS buffer, is added to the medium plate for overnight incubation at 4° C. This is followed by regaining the extracted buffer from the medium plate to carry out a process of centrifugation at 14170×g for 30 minutes, filtration with 0.22 μl of filter, and incubation with DNase I for 1 hour sequentially to completely exclude the debris, germs and bacterial nucleic acid and obtain a bacteriophage suspension. Next, polyethylene glycol 8000 (PEG-8000; Sigma) and NaCl are added separately to the bacteriophage suspension to provide the final concentration of 3% PEG-8000 and 0.33M respectively, followed by keeping at 4° C. for 1 hour and centrifugation at 4° C., 14170×g for 30 minutes to take the precipitation of the bacteriophage suspension. As a result, a purified bacteriophage of the present invention is finally obtained via a repeated process of CsCl gradient separation by loading the precipitation on top of the CsCl gradient (1.3, 1.5 or 1.7 g/ml), centrifugating at 35000 rpm at 4° C. for 9 hours and dialyzing with a PBS buffer. The purified bacteriophage will be stored at 4° C. for a follow-up use. In the preferable embodiment of the present invention, the purified bacteriophage is passed through a Detoxi-Gel™ endotoxin removing gel (Pierce Biotechnology; Rockford) before the storage, for the sake of removing the remaining endotoxins from the bacteriophage suspension.

Figure 2:
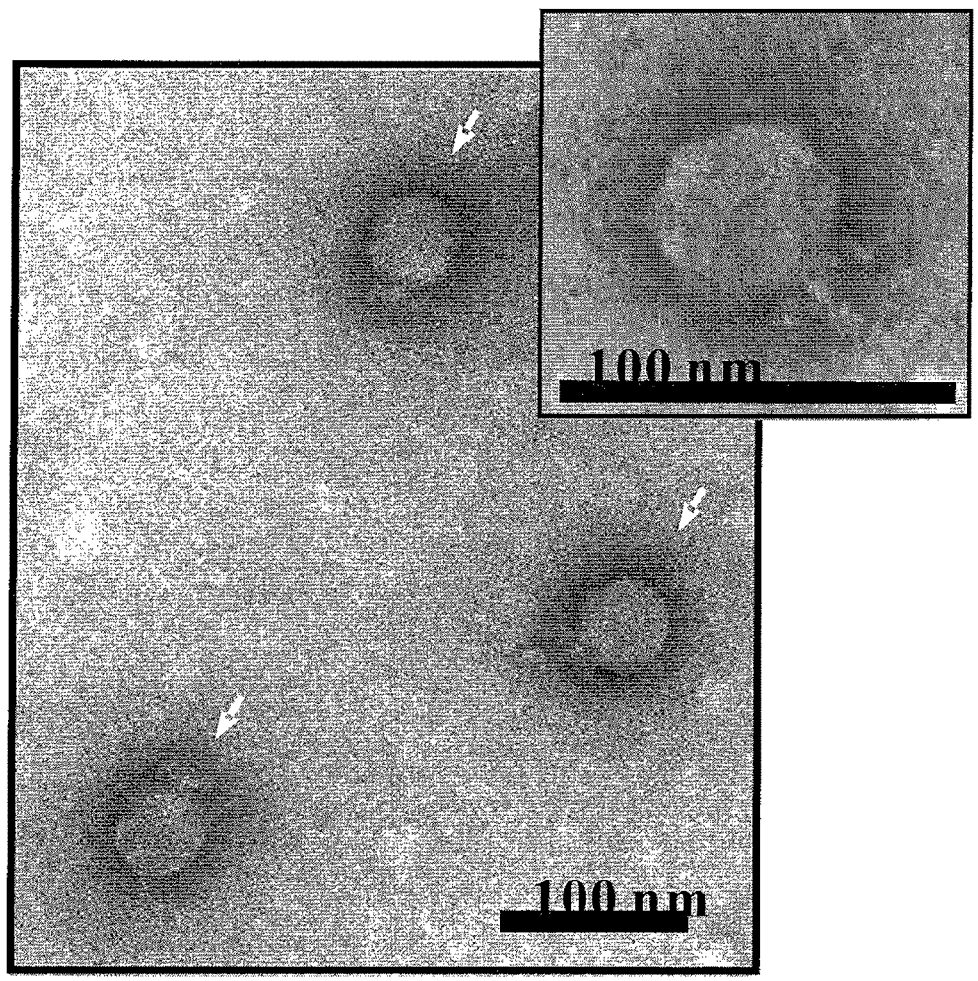
FIG. 2 is a TEM photo of the viral particles of the newly isolated lytic bacteriophage in the present invention.
Figure 3:
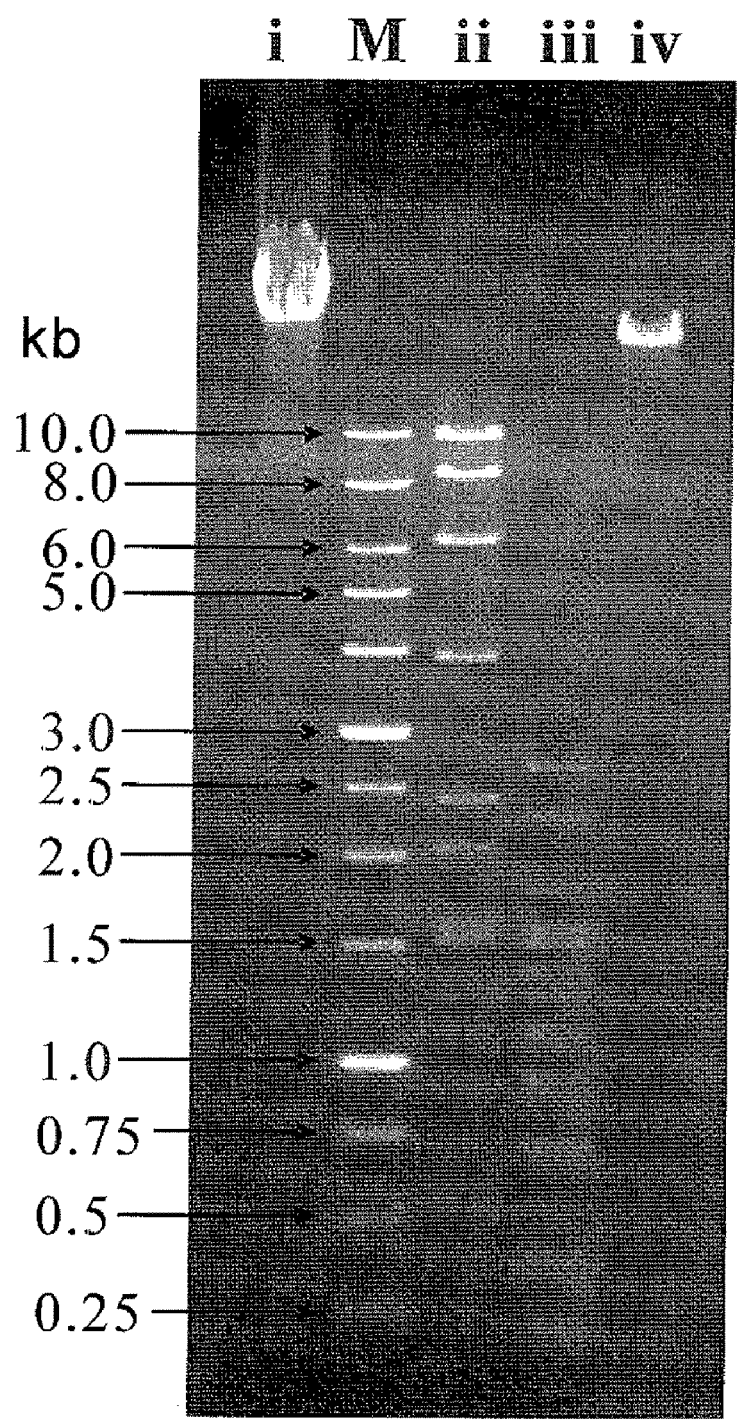
FIG. 3 is a photo of the gel electrophoresis of the newly isolated lytic bacteriophage in the present invention.
Figure 4:
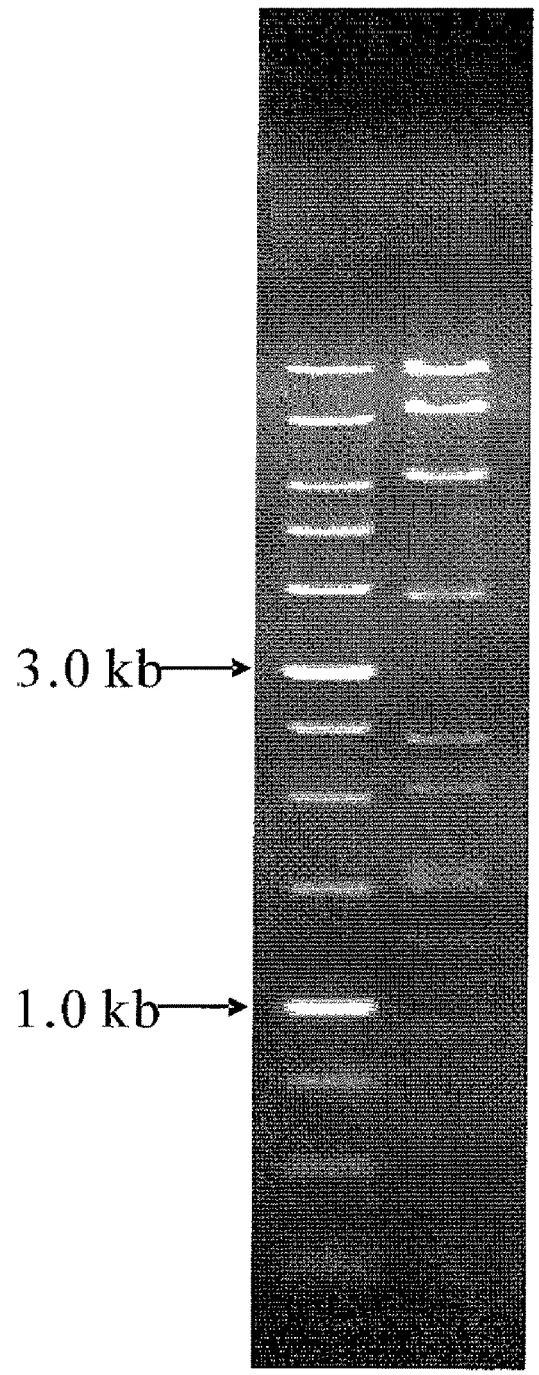
FIG. 4 is another photo of the gel electrophoresis of the newly isolated lytic bacteriophage in the present invention.

In the step of "identification S3," the purified bacteriophage is analyzed by a transmission electron microscope (TEM) and restriction enzymes. With reference to the FIG. 2, the morphology of the purified bacteriophage in the present invention examined using a JEM-2000 EX II electron microscope (JEOL; Japan), demonstrates a plurality of regular hexahedral particles under a 80000× view with an approximate size of 46.5 nm, wherein the particles further comprise a tiny tail of around 13.2 nm in length and 5.4 nm in width. Moreover, as it is shown in FIGS. 3 and 4, the nucleotide sequence of the purified bacteriophage shows several different fragments in various sizes after the digestion of endonuclease EcoRV (ii), HincII (iii) and XbaI (iv) respectively, in comparison with the untreated bacteriophage fragment (i) and a commercial DNA marker (M). Accordingly, the purified bacteriophage of the present invention is around 40.5 kbs in full-size. Hence, according to The Database of the International Committee on Taxonomy of Virus, also named ICTVdB, the bacteriophage of the present invention is classified as a phage of Podoviridae, and deposited at DSMZ-Deutsche Sammlung von Mikroorganismen und Zellkulturen with deposit number DSM 24329.

To further indicate the lytic ability of the bacteriophage in the present invention, an infectious test specific to a clinical strain of *K. pneumoniae* is performed either in an in vitro or in vivo model, wherein the *K. pneumoniae* is isolated from a patient with *K. pneumoniae* infection complicated by primary liver abscess and bacteremia at the National Cheng-Kung University Hospital in Taiwan, and deposited at DSMZ-Deutsche Sammlung von Mikroorganismen und Zellkulturen with deposit number DSM 24328.

As summarized in Table 1, the bacteriophage (DSM 24329) of the present invention are distributed by titers into 4 groups, including a, b, c and d (as a control group), and further inoculated to a overnight culture of K pneumoniae cells individually (with titer of $7\times10^7$ CFU/mL), wherein the titer of the *K. pneumoniae* cells and bacteriophage in each group (a to d) are monitored and recorded during the test.

TABLE 1

The multiplicity of infection (MOI) of the bacteriophage in each group

| Groups | MOI of the bacteriophage |
|---|---|
| a | 0.01 |
| b | 0.1 |
| c | 1 |
| d | — |

Figure 5:
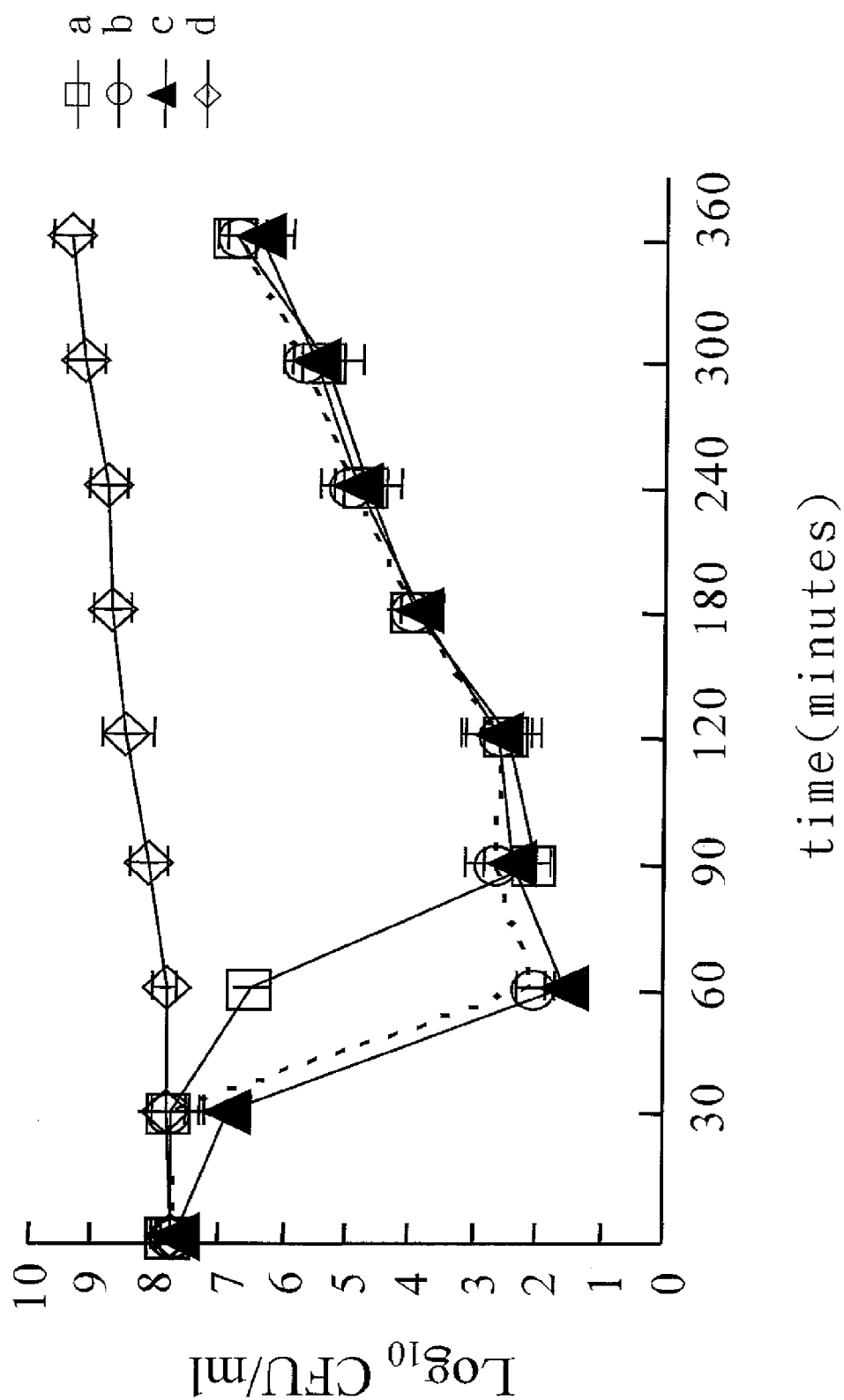
FIG. 5 is a line chart illustrating the infection of the newly isolated lytic bacteriophage to *K. pneumoniae* under the in vitro model.

With reference to FIG. 5, the titer of the control group (d) is maintained at about $7\times10^7$ CFU/mL. In contrast, the titers of groups a, b and c decrease sharply to around $10^{2\sim3}$ CFU/mL within 90 minutes. It is suggested that the bacteriophage of the present invention strongly shows the lytic effects on the *K. pneumoniae* cells, by infecting the *K. pneumoniae* cells and lysing the cell wall of the *K. pneumoniae* so as to significantly decrease the titer of the *K. pneumoniae* cells in a short time. In addition, the lytic effects of the bacteriophage will not decline even with a lower dose, for example MOI=0.01. Thus, it is believed that the bacteriophage of the present invention is specifically infectious to the *K. pneumoniae* cells, which can lead to the lysis and death of the *K. pneumoniae* cells under an in vitro model.

Figure 6:
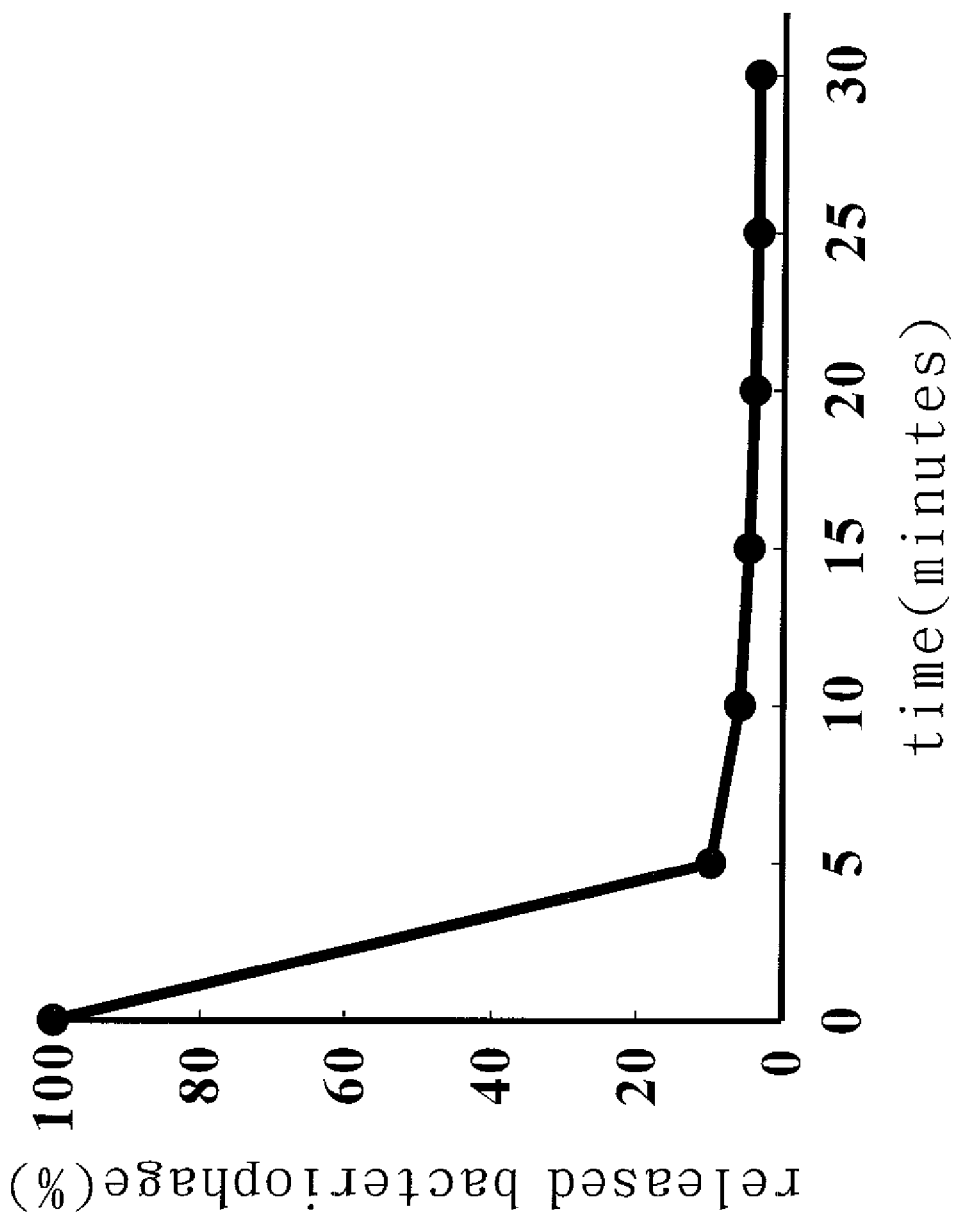
FIG. 6 is a line chart illustrating the absorption time of the lytic bacteriophage to hosts under the in vitro model.
Figure 7:
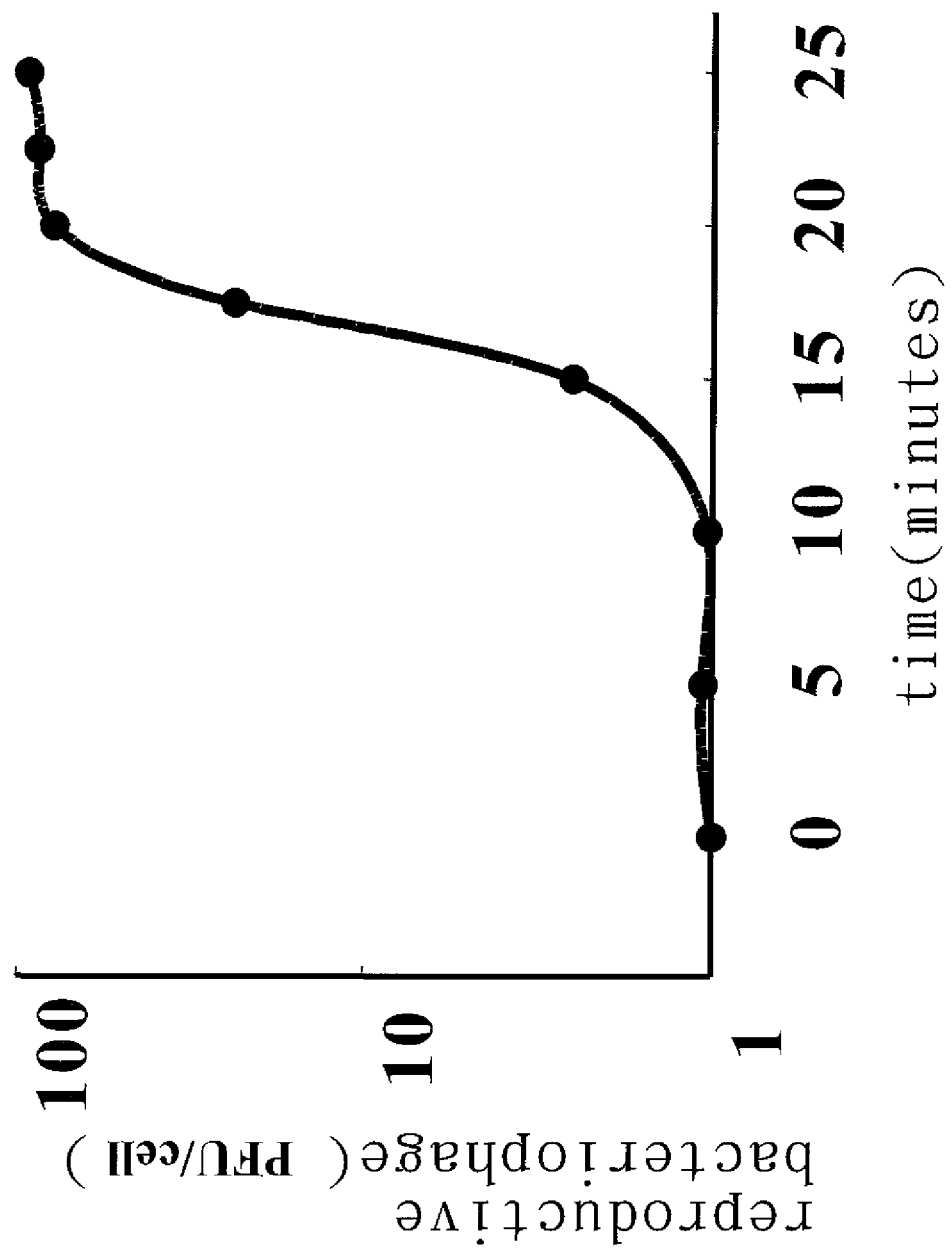
FIG. 7 is a line chart illustrating the reproductive rate of the lytic bacteriophage in the present invention.

Referring to FIGS. 6 and 7, in accordance with the above infectious examination, approximately 90% of the bacteriophage in the present invention has adsorbed to the *K. pneumoniae* cells within 5 minutes of the incubation. Also, the adsorption rate of the bacteriophage rises to around 97% in 15 minutes. Moreover, an increasing amount of the reproductive bacteriophage is released from the *K. pneumoniae* cells 10 minutes after the infection. It is suggested that the bacteriophage of the present invention shows efficient adhesion and lysis on the *K. pneumoniae* cells, by rapidly absorbing and invading the *K. pneumoniae* for reproduction, and further lysing and releasing the reproductive bacteriophage in a short time. It is believed that the bacteriophage of the present invention is sufficient to inhibit the development of the *K. pneumoniae* cell in vitro.

With reference to Table 2, the bacteriophage (DSM 24329) of the present invention are further inoculated to 6 groups of mice having had intragastric treatment of *K. pneumoniae* (DSM 24328) in advance, comprising a group of negative control (I) with *K. pneumoniae* infection only, a group of positive control (VI) with bacteriophage treatment only, and groups II to V sharing different doses of bacteriophage treatment and *K. pneumoniae* infection. In the present invention, the mortality of the mice in each group (including I to VI) is observed and recorded during the test.

TABLE 2

The titer of *K. pneumoniae* and bacteriophage in each group

| groups | MOI of the bacteriophage | Titer of *K. pneumoniae* (CFU/mouse) |
|---|---|---|
| I | — | $2 \times 10^8$ |
| II | 0.001 | $2 \times 10^8$ |
| III | 0.01 | $2 \times 10^8$ |
| IV | 0.1 | $2 \times 10^8$ |
| V | 1 | $2 \times 10^8$ |
| VI | 1 | — |

Figure 8:
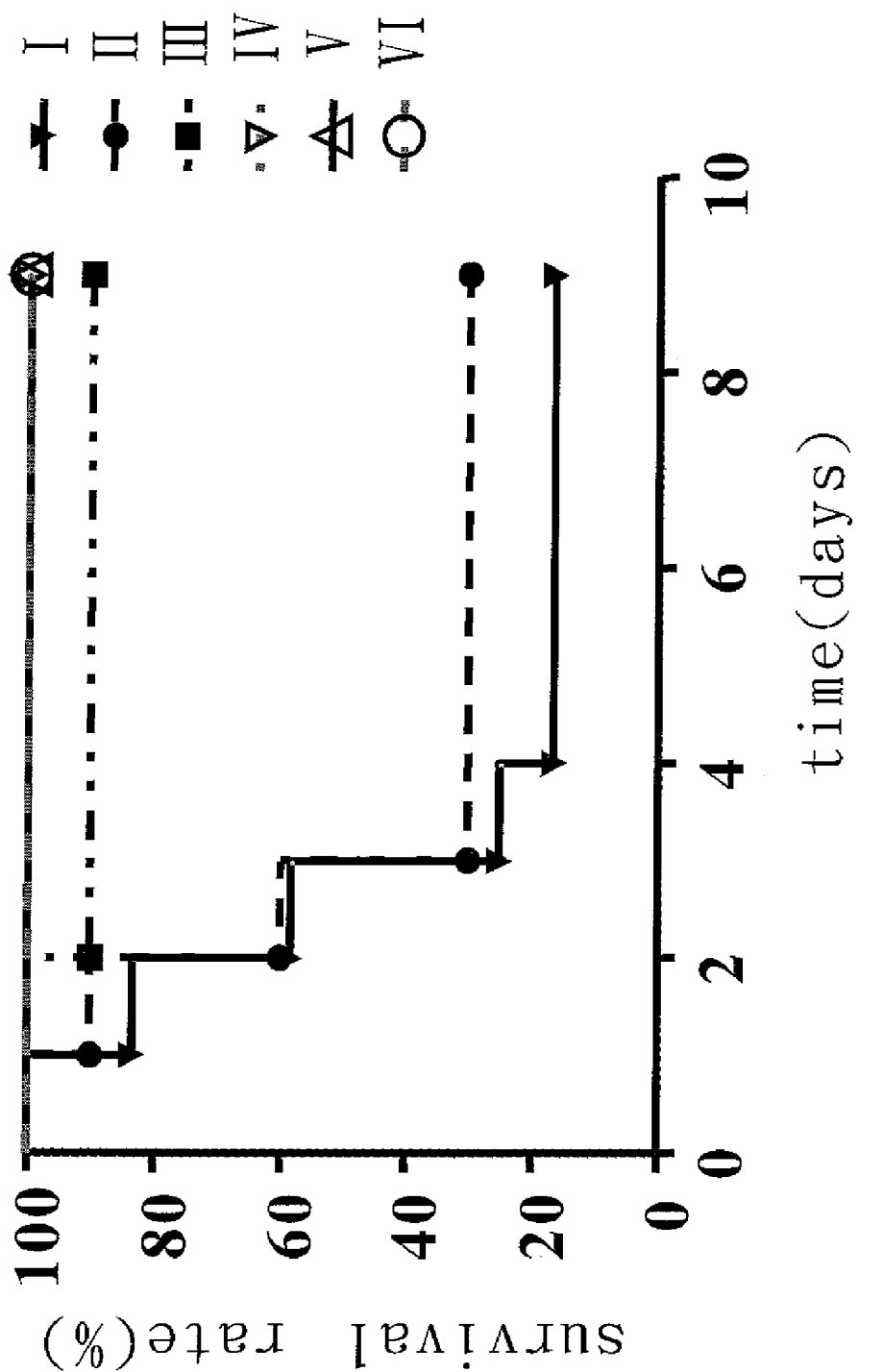
FIG. 8 is a line chart illustrating the infection of the lytic bacteriophage to *K. pneumoniae* under the in vivo model.

According to FIG. 8, around 90% of mice will die in 4 days after the treatment of *K. pneumoniae* (as shown in I curve). However, the risk of *K. pneumoniae* induced death can be significantly reduced by the bacteriophage of the present invention in a positive dose-dependent manner, wherein the mice have treatments of $2 \times 10^6$ (MOI=0.01), $2 \times 10^7$ (MOI=0.1) and $2 \times 10^8$ (MOI=1) PFU/mouse bacteriophage respectively, resulting in approximately 90% of survival in the present invention (see the III, IV, V curve). It is suggested that the bacteriophage of the present invention is specifically targeted to the *K. pneumoniae* but completely safe for animals generally. Hence, the bacteriophage of the present invention is sufficient to prevent the death caused by *K. pneumoniae* infection in mice, especially even with low dose of bacteriophage treatment.

In summary, the bacteriophage (DSM 24329) of the present invention is proved to be specifically infectious to the *K. pneumoniae* in Taiwan, showing strong and efficient lytic effects on the *K. pneumoniae* cells. Therefore, the bacteriophage of the present invention has potential to be developed as a therapeutic and prophylactic medication/disinfectant for treating *K. pneumoniae* infection in Taiwan, and can be manufactured into any type of medication/disinfectant such as liquid, tablet or ointment, for direct application or as an accompaniment to one or more acceptable antibiotics, reagent, substrate or other therapeutic factors via an oral approach or injection. In this situation, the invasive *K. pneumoniae* infection in Taiwan can be dramatically suppressed so that the severe complications of liver abscess and bacteremia can be relieved.

Through the present invention, a newly isolated lytic bacteriophage which is deposited at DSMZ-Deutsche Sammlung von Mikroorganismen and Zellkulturen with deposit number DSM 24329 specifically targeted to the *K. pneumoniae* (DSM 24328) in Taiwan is isolated from a Taiwanese hospital, showing efficient infection and lytic effects on *K. pneumoniae* cells in either in vitro or in vivo models. Therefore, it is sufficient to be put to use on the development of medication or disinfectant adapted to the therapy or prophylaxis of invasive *K. pneumoniae* infections.

Although the invention has been described in detail with reference to its presently preferred embodiment, it will be understood by one of ordinary skill in the art that various modifications can be made without departing from the spirit and the scope of the invention, as set forth in the appended claims.

What is claimed is:

1. A newly isolated lytic bacteriophage specifically against *Klebsiella pneumoniae*, with the deposit number (DSM 24329), which shows broad host ranges and lytic effects on the *K. pneumoniae* isolated from Taiwan either in in vivo or in vitro models wherein a nucleotide sequence of the said newly isolated lytic bacteriophage comprises a plurality of EcoRV sites.

2. The newly isolated lytic bacteriophage specifically against *Klebsiella pneumoniae* as defined in claim 1, wherein the infectious titer of the newly isolated lytic bacteriophage to the *K pneumoniae* is $7 \times 10^{5 \sim 7}$ (PFU/ml).

3. The newly isolated lytic bacteriophage specifically against *Klebsiella pneumoniae* as defined in claim 1, wherein the infectious titer of the newly isolated lytic bacteriophage to the *K. pneumoniae* is $2 \times 10^{5 \sim 8}$ (PFU/mouse).

4. The newly isolated lytic bacteriophage specifically against *Klebsiella pneumoniae* as defined in claim 1, wherein the newly isolated lytic bacteriophage belongs to the family of Podoviridae.

5. The newly isolated lytic bacteriophage specifically against *Klebsiella pneumoniae* as defined in claim 1, wherein the newly isolated lytic bacteriophage is 40.5 kbs in full-size.

6. The newly isolated lytic bacteriophage specifically against *Klebsiella pneumoniae* as defined in claim 1, wherein the nucleotide sequence thereof comprises a plurality of HincII sites.

7. The newly isolated lytic bacteriophage specifically against *Klebsiella pneumoniae* as defined in claim 1, wherein the nucleotide sequence thereof comprises an XbaI site.

8. The newly isolated lytic bacteriophage specifically against *Klebsiella pneumoniae* as defined in claim 1, wherein the nucleotide sequence thereof comprises 11 EcoRV sites, with 10.0 kb, 8.5 kb, 6.2 kb, 3.9 kb, 2.4 kb, 2.1 kb, 1.7 kb, 1.6 kb, 1.3 kb, 0.9 kb, 0.6 kb, and 0.5 kb between each two adjacent sites respectively.

9. The newly isolated lytic bacteriophage specifically against *Klebsiella pneumoniae* as defined in claim 1, wherein the morphology of said bacteriophage comprises regular hexahedral particles when viewed under transmission electron microscopy.

* * * * *